(12) United States Patent  (10) Patent No.: US 8,273,073 B2
Levine et al.  (45) Date of Patent: *Sep. 25, 2012

(54) LONG NOSE MANIPULATABLE CATHETER

(75) Inventors: Marc-Alan Levine, Pottstown, PA (US); Stephen Hebert, Berkeley, CA (US)

(73) Assignee: Micrus Endovascular Corporation, San Jose, CA (US)

( * ) Notice: Subject to any disclaimer, the term of this patent is extended or adjusted under 35 U.S.C. 154(b) by 225 days.

This patent is subject to a terminal disclaimer.

(21) Appl. No.: 12/554,588

(22) Filed: Sep. 4, 2009

(65) Prior Publication Data
US 2009/0326484 A1 Dec. 31, 2009

Related U.S. Application Data

(63) Continuation of application No. 10/678,008, filed on Oct. 1, 2003, now Pat. No. 7,591,813.

(51) Int. Cl.
A61M 25/00 (2006.01)
(52) U.S. Cl. ....................................................... 604/528
(58) Field of Classification Search .......... 604/523–528, 604/101.01, 103.1, 264, 95.01, 95.04; 600/585
See application file for complete search history.

(56) References Cited

U.S. PATENT DOCUMENTS

| 4,545,390 A | 10/1985 | Leary |
| 4,586,923 A | 5/1986 | Gould et al. |
| 4,723,936 A | 2/1988 | Buchbinder et al. |
| 4,739,768 A | 4/1988 | Engelson |
| 4,813,934 A | 3/1989 | Engelson et al. |
| 4,884,579 A | 12/1989 | Engelson |
| 4,960,411 A | 10/1990 | Buchbinder |
| 4,983,169 A | 1/1991 | Furukawa |
| 4,994,069 A | 2/1991 | Ritchart et al. |
| 5,234,416 A * | 8/1993 | Macaulay et al. ............ 604/527 |
| 5,431,168 A | 7/1995 | Webster, Jr. |
| 5,437,632 A | 8/1995 | Engelson |
| 5,487,757 A * | 1/1996 | Truckai et al. ................ 604/264 |
| 5,497,783 A | 3/1996 | Urick et al. |
| 5,499,973 A | 3/1996 | Saab |
| 5,507,725 A | 4/1996 | Savage et al. |
| 5,911,715 A | 6/1999 | Berg et al. |
| 5,968,012 A | 10/1999 | Ren et al. |
| 6,083,222 A | 7/2000 | Klein et al. |
| 6,123,699 A * | 9/2000 | Webster, Jr. .................. 604/528 |
| 6,251,092 B1 | 6/2001 | Qin et al. |

(Continued)

FOREIGN PATENT DOCUMENTS
EP 0254701 A1 1/1988
(Continued)

*Primary Examiner* — Christopher D Koharski
(74) *Attorney, Agent, or Firm* — Gregory & Sawrie LLP

(57) ABSTRACT

A long nose manipulatable catheter is described herein. The catheter generally comprises a flexible joint region defining a main lumen and an adjacent wire lumen. The wire lumen has an opening near or at a distal end of the flexible joint region and a push/pull wire can be pushed or pulled through the wire lumen. The catheter assembly may also comprise at least one radio-opaque marker band for securing the push/pull wire. The joint region has a predetermined length sized to affect a flexure of the joint and is generally located at the distal end of the catheter. The joint region itself may be varied to extend distally from where the braid terminates, or it may extend to encompass a portion of the braid. By varying a length of the joint region, the amount of curvature and flexure of the joint region can be controlled.

6 Claims, 10 Drawing Sheets

U.S. PATENT DOCUMENTS

| | | |
|---|---|---|
| 6,270,476 B1 | 8/2001 | Santoianni et al. |
| 6,321,749 B1 | 11/2001 | Toti et al. |
| 6,482,221 B1 | 11/2002 | Hebert et al. |
| 6,544,215 B1 | 4/2003 | Bencini |
| 6,726,700 B1 | 4/2004 | Levine |
| 6,976,991 B2 | 12/2005 | Hebert et al. |
| 2001/0039412 A1 | 11/2001 | Fariabi |
| 2002/0026145 A1 | 2/2002 | Bagaoisan et al. |
| 2002/0165571 A1 | 11/2002 | Hebert et al. |
| 2002/0177867 A1 | 11/2002 | Hebert et al. |
| 2003/0236492 A1 | 12/2003 | Honebrink |
| 2003/0236493 A1 | 12/2003 | Mauch |
| 2005/0075661 A1 | 4/2005 | Levine |

FOREIGN PATENT DOCUMENTS

| | | |
|---|---|---|
| EP | 1389478 | 2/2004 |
| EP | 1685870 | 8/2006 |
| WO | WO 02/15972 | 2/2002 |

\* cited by examiner

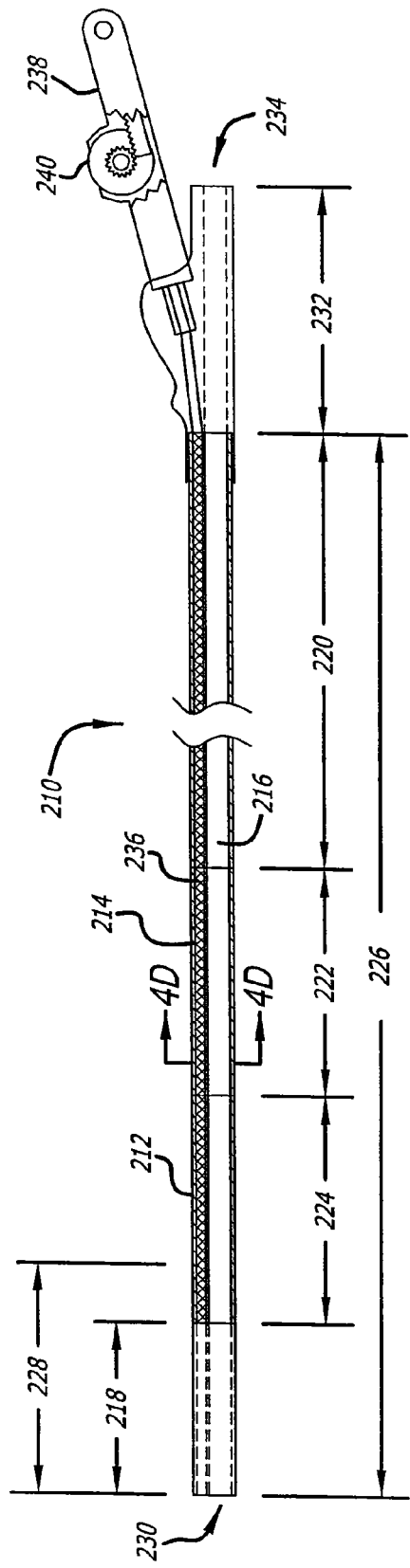
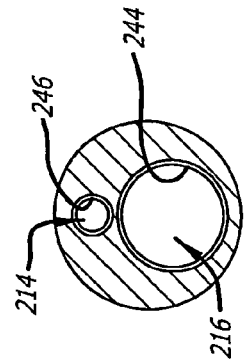
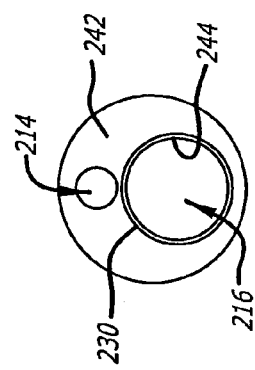
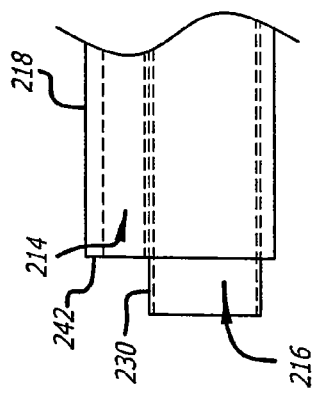
FIG. 4A
FIG. 4B
FIG. 4C
FIG. 4D

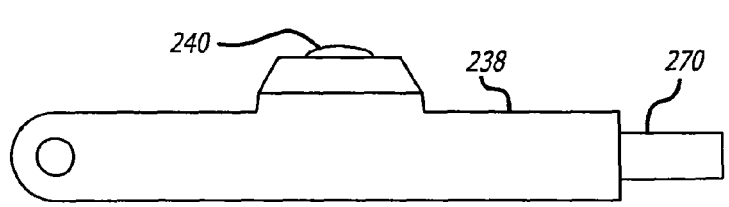
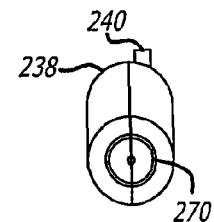
FIG. 7A  FIG. 7B
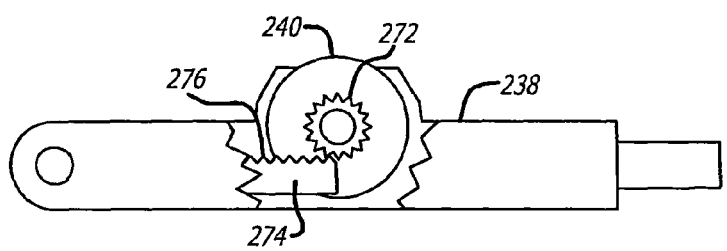
FIG. 7C
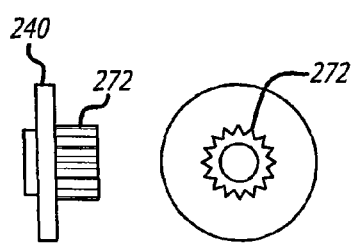
FIG. 7D
FIG. 7E

LONG NOSE MANIPULATABLE CATHETER

This is a continuation of application Ser. No. 10/678,008, filed Oct. 1, 2003, now U.S. Pat. No. 7,591,813.

FIELD OF THE INVENTION

The invention is generally in the field of intravascular devices. More particularly, it relates to intravascular catheters having a flexible and manipulatable hinge or joint region. The delivery lumen may be also used for placement of occlusive materials, e.g., in an aneurysm.

BACKGROUND OF THE INVENTION

Endovascular therapy has been used to treat different conditions, such treatments including control of internal bleeding, occlusion of blood supply to tumors, and occlusion of aneurysm. Often the target site of the malady is difficult to reach. Because of their ability to access remote regions of the human body and deliver diagnostic or therapeutic agents, catheters are increasingly becoming components of endovascular therapies. Generally, catheters are introduced into large arteries, such as those in the groin or in the neck, and then pass through narrowing regions of the arterial system until the catheter's distal tip reaches the selected delivery site. To be properly utilized, catheters are often stiffer at their proximal end to allow the pushing and manipulation of the catheter as it progresses through the body but sufficiently flexible at the distal end to allow passage of the catheter tip through the body's blood vessels without causing significant trauma to the vessel or surrounding tissue.

Microcatheters, such as those shown in U.S. Pat. Nos. 4,884,579 and 4,739,768, each to Engleson, allow navigation through the body's tortuous vasculature to access such remote sites as the liver or the cerebral arteries of the brain. Although other methods of causing a catheter to proceed through the human vasculature exist (e.g., flow directed catheters), a guidewire-aided catheter is considered to be both quicker and more accurate than other procedures. Catheters with deflectable or variable stiffness distal ends (which increase the flexibility of the catheter's distal end) have been disclosed in U.S. Pat. No. 6,083,222, to Klein et al; U.S. Pat. No. 4,983,169, to Furukawa; U.S. Pat. No. 5,499,973, to Saab; and U.S. Pat. No. 5,911,715, to Berg et al.

The addition of a fluid-expandable balloon on the distal end of the catheter and a coupler on the proximal end allows various percutaneous medical treatments such as pressure monitoring, cardiac output and flow monitoring, angioplasty, artificial vaso-occlusion, and cardiac support. Balloon catheters generally include a lumen that extends from the proximal end and provides fluid to the balloon for inflation. Examples of balloon catheters are disclosed in U.S. Pat. No. 4,813,934 to Engleson et al and U.S. Pat. No. 5,437,632 to Engelson et al. A balloon catheter with an adjustable shaft is shown in U.S. Pat. No. 5,968,012, to Ren et al.

For certain vascular malformations and aneurysms, it may be desirable to create an endovascular occlusion at the treatment site. A catheter is typically used to place a vaso-occlusive device or agent within the vasculature of the body either to block the flow of blood through a vessel by forming an embolus or to form such an embolus within an aneurysm stemming from the vessel. Formation of an embolus may also involve the injection of a fluid embolic agent such as microfibrillar collagen, Silastic beads, or polymeric resins such as cyanoacrylate. Ideally, the embolizing agent adapts itself to the irregular shape of the internal walls of the malformation or aneurysm. Inadvertent embolism due to an inability to contain the fluid agent within the aneurysm is one risk which might occur when using fluid embolic agents.

Mechanical vaso-occlusive devices may also be used for embolus formation. A commonly used vaso-occlusive device is a wire coil or braid which may be introduced through a delivery catheter in a stretched linear form and which assumes an irregular shape upon discharge of the device from the end of the catheter to fill an open space such as an aneurysm. U.S. Pat. No. 4,994,069, to Ritchart et al, discloses a flexible, preferably coiled, wire for use in a small vessel vaso-occlusion. Some embolic coils are subject to the same placement risks as that of fluid embolic agents in that it is difficult to contain the occlusive coil within the open space of the aneurysm.

Another example of a steerable catheter is disclosed in U.S. Pat. No. 4,723,936, to Buchbinder et al. Buchbinder describes a steerable catheter having a spring coil body defining a lumen and a deflection wire extending through the catheter. The deflection wire is positioned either inside or outside the spring coil body but is not contained within a separate wire lumen.

U.S. Pat. No. 4,960,411, also to Buchbinder, discloses a steerable catheter device having a deflection wire within a separate wire lumen. The distal end of the wire lumen is a closed end and has the distal end of the deflection wire embedded therein.

U.S. Pat. No. 6,251,092, to Qin et al., discloses a deflectable guiding catheter similarly having a deflection wire or member contained within a lumen. The distal end of the wire lumen is similarly closed and has the distal end of the deflection member embedded therein.

U.S. Pat. No. 6,321,749, to Toti et al., discloses an endotracheal tube which is manipulatable via a tensioning wire within a lumen. The wire is exposed within an open area of the tube and is used in conjunction with a variety of biased deflection members to assist in manipulating the tube.

However, none of the above-mentioned devices discloses an intravascular device having a small diameter, highly flexible construction which permits movement along a small-diameter, tortuous vessel path, and having a flexible method of placement to ensure accuracy, as disclosed herein.

SUMMARY OF THE INVENTION

A catheter or catheter section described below may be utilized for negotiating movement along small-diameter, tortuous vessels. The catheter may comprise a flexible joint region which defines a main lumen and an adjacent wire lumen therethrough, the wire lumen having an opening near or at a distal end of the flexible joint region; a push/pull wire configured to be pushed or pulled along a longitudinal axis of the wire through the wire lumen; and wherein the flexible joint region has a predetermined length sized to affect a flexure of the flexible joint region. Moreover, the catheter assembly may further comprise at least one radio-opaque marker band near or at the distal end of the flexible joint region for securing the push/pull wire thereto, wherein the flexible joint region has a predetermined length sized to affect a flexure of the flexible joint region.

An inflatable balloon member may optionally be used with the catheter assembly. If the inflatable member is utilized, the flexible joint may variously be distal of the inflatable member, within the inflatable member, or proximal of said inflatable member.

One particular variation of the catheter assembly may have a catheter body which defines a main lumen through the length of the assembly. A push/pull wire lumen having an open distal end may also be defined through the length of the catheter body, or at least through a majority of the length of catheter body, extending from a fitting at a proximal end of the catheter assembly to a region near or at the distal end of the device. The catheter body itself may be comprised of several regions each having a different degree of flexibility. For instance, the catheter assembly may comprise a first portion distal of the fitting having a first stiffness. A second portion, having a second stiffness and located distal of the first portion, may be more flexible relative to the first portion. Likewise, a third portion, having a third stiffness and located distal of the second portion, may be more flexible relative to the first and second portions. Thus, the catheter body may have a length comprised of progressively more flexible sections the farther distally located along the catheter. Distal to the third section, bending portion or flexible joint region may be positioned, as described in further detail below.

The push/pull wire lumen may include a braided ribbon integrated throughout the length of the lumen. Alternatively, the braided ribbon may be integrated through the lumen to terminate proximally of the joint region. The braided ribbon may be a uniform braid or it may be braided with a varying braid pitch. The braided ribbon may be made from a number of materials. For instance, metals which are members of a class of alloys known as super-elastic alloys may be utilized for the braid material.

The manipulatable or flexible joint region is generally located at the distal end of the catheter body and is configured to bend when manipulated by the push/pull wire. The bending portion itself may be varied to extend to where the braid terminates, or it may be extended to the bending portion to encompass a portion of the braid. By varying the length of the flexible joint region, the amount of curvature and flexure of the joint region can be controlled. For instance, a joint region having a relatively shortened length between the distal end of the joint region and the terminal end of the braid may allow for a reduced degree of flexure relative to a neutral position of the catheter. In comparison, a lengthened joint region extending to a more proximally located terminal end may allow for a relatively greater degree of flexure. Accordingly, the degree of flexure may be controlled in part by the length of the flexible joint region. Thus, the flexible region may be flexed up to 90° relative to the longitudinal axis of the catheter assembly and in some cases, the flexible region may be flexed up to 180° relative to the longitudinal axis depending upon the length of the flexible joint region. To further facilitate bending of the catheter, additional members such as coils may be incorporated into the device, for instance in the transitional region, to aid in further controlling the bending of the joint region.

BRIEF DESCRIPTION OF THE DRAWINGS

FIG. 4A shows a cross-sectional side view of another variation of a catheter assembly.

FIG. 4B shows a detail side view in which a portion of the tubing defining the main lumen extends as an extension past a distal face of the joint region.

FIG. 4C shows end view of flexible joint region of FIG. 4B.

FIG. 4D shows a cross-sectional end view of the catheter body illustrating the wire lumen and the main lumen.

FIGS. 7A to 7C show side, end, and partially removed side views, respectively, of one variation of a control handle for manipulating the push/pull wire.

FIGS. 7D and 7E show detail views of the wheel and rack, respectively, which may be used to manipulate the push/pull wire.

DETAILED DESCRIPTION OF THE INVENTION

This invention involves a multi-lumen catheter for the delivery of vaso-occlusive materials or implants. The device may optionally include a balloon member. The device is shown in detail in the figures wherein like numerals indicate like elements. The catheter preferably includes a shapeable, flexible distal section which may be in the vicinity of the balloon, if the balloon member is utilized. The flexible section, or "hinge region", preferably is manipulated from outside the body during the process of delivering the vaso-occlusive device or material. The terms "hinge region", "hinge", or "flexible joint" may be used interchangeably.

Figure 1A:
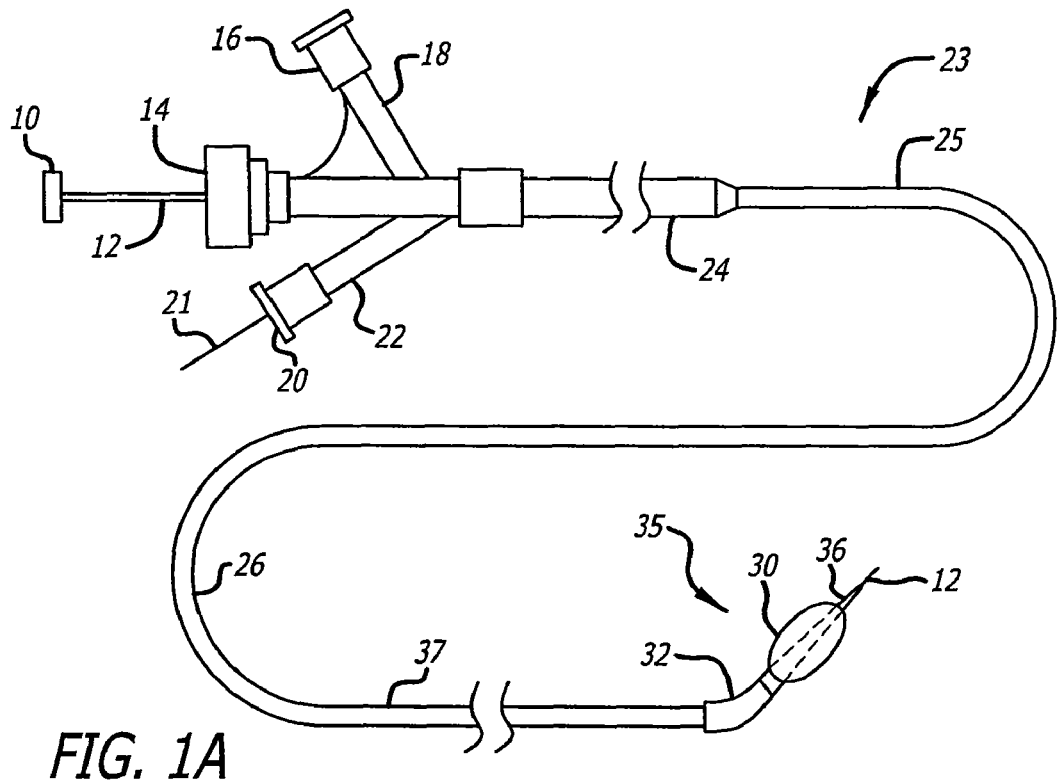
FIG. 1A shows an external view of one variation of the catheter assembly.

FIG. 1A shows a catheter assembly 23 made according to one variation of the invention. This variation of the catheter assembly 23 includes a catheter shaft 25 composed of a flexible, thin walled body or tube 26 having an inner lumen which extends between proximal and distal catheter ends 24, 37, respectively. The tube 26 is preferably a generally nondistensible polymer having the appropriate mechanical properties for this application, and preferably polyethylene (e.g., HDPE, LDPE, LLDPE, MDPE, etc.), polyesters (such as Nylon), polypropylene, polyimide, polyvinyl chloride, ethylvinylacetate, polyethylene terephthalate, polyurethane (e.g., TEXIN such as that made by Bayer Corporation), PEBAX, fluoropolymers, mixtures of the aforementioned polymers, and their block or random co-polymers.

The catheter assembly may be utilized for access through the vasculature to the brain often, but not necessarily, using a guide wire. If an optional balloon member is included in the catheter assembly, the balloon member may be inflated to close or to restrict any hollow body lumen, such as an artery, vein, orifice, cavity, etc., or the mouth of an aneurysm prior to or during placement of a vaso-occlusive device. Generally, the assembly may be flexed at a "hinge region" near or at the distal end of the catheter by a push/pull wire extending proximally through the catheter. A main lumen defined through the catheter assembly may be utilized for the introduction of a vaso-occlusive device or material for eventual placement in the vasculature.

The proximal catheter end 24 may be provided with a fitting 18 (e.g., a "LuerLok") through which fluid may be supplied to the catheter's inflation lumen through a side port 16. The proximal end of the catheter is provided with a second port 20 and a fitting 22 through which the push/pull wire may be used to manipulate the hinge region 32 in the distal catheter tip. The proximal end fitting 18 includes an axially extending port 14 which communicates with the catheter's delivery/guide wire lumen. The optional guide wire 12 may have any suitable construction for guiding the flexible catheter to its intended site within the body. The proximal end of the guidewire 12 may be equipped with a handle 10 for applying torque to the guidewire 12 during catheter operation, as described in further detail below. The guidewire may have a variable stiffness or stepped diameter along its length which typically, e.g., a larger-diameter, stiffer proximal region and one or more smaller-diameter, more flexible distal regions.

The distal portion 35 of the catheter may include an optional inflatable member 30, typically a balloon. An opening 36 at the distal end of the catheter may also be used for delivery of drugs and/or vaso-occlusive devices to a preselected vascular site. The distal end region 35 of the catheter 25 may be provided with-an inflatable balloon 30 which, when inflated, may aid in the placement of vaso-occlusive materials or devices by blocking the entrance to the aneurysm or the artery adjacent to the aneurysm. An example of a catheter assembly which incorporates a balloon member with a flexible joint is disclosed in further detail in U.S. patent application Ser. No. 09/643,085 filed Aug. 21, 2000, which is co-owned and incorporated herein by reference in its entirety.

Figure 1B:
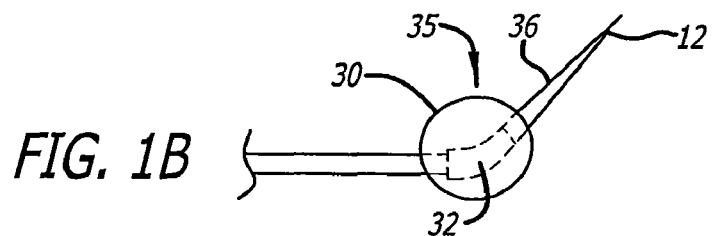
FIGS. 1B and 1C show alternative configurations of the distal region of the catheter assembly.
Figure 1C:
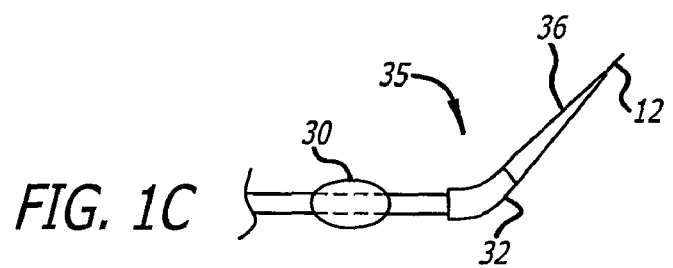

Although a balloon member is illustrated in several variations, use of the balloon member is merely optional. The balloon wall section (discussed in greater detail below) is preferably formed from a thin sleeve of polymeric material and attached at its opposite sleeve ends to a relatively more rigid tube section. FIGS. 1A, 1B, and 1C display various configurations of the distal catheter tip 35 positioning based on the placement of the flexible hinge region. FIGS. 1A, 1B, and 1C, respectively, show variations of the inventive catheter 23 in which the hinge region 32 is placed proximal to (FIG. 1A), within (FIG. 1B), and distal to (FIG. 1C) the inflatable member region 30 if such an inflatable member 30 were included in the catheter assembly. Flexion of the hinge region may be achieved through remote manipulation of the push/pull wire 21.

FIGS. 2A through 2D illustrate variations of the distal end region 35 and hinge region 32 of the catheter illustrated in FIG. 1A, 1B, and 1C. The catheter tube 40 of FIG. 2A may have an inflatable member 44, e.g., a balloon, formed by an inflatable sleeve secured at its ends 41, 43 to the catheter tube wall 40. The inflatable member or balloon 44 may be of a shape, thickness, and material as is typical of balloons used in neurovascular balloon catheters. Preferably, though, the inflatable member or balloon 44 may be formed of a thin polymeric material, and preferably an elastomeric, stretchable material such as silicone rubber, latex rubber, polyvinyl chloride, complex co-polymers such as styrene-ethylene butylene-styrene copolymers such as C-FLEX, or alternatively, a non-stretchable film material such as polyethylene, polypropylene, or polyamides such as Nylon. Attachment of the sleeve ends to the catheter tube may be by adhesives, heat shrinkage, mechanical fasteners, or other suitable method. Inflation lumen 42, which is also optional if balloon 44 is included in the assembly, allows communication between the inflation fluid source and the balloon 44 through at least one opening 50 formed in the catheter tube 40. Inflation and deflation of the balloon are effected by the passage of radio-opaque fluid, saline, or other fluid. A push/pull wire lumen 60 may extend throughout the catheter tube 40 to protect the passage of the push/pull wire 62. To assist in preventing collapse of the tube 60 enclosing the push/pull wire 62 and to prevent kinking or bulging during actuation, the push/pull wire lumen 60 may have additional structure preferably provided by a layer of higher stiffness polymer (e.g., a polyimide), a support coil, or a support braid, as described in further detail below.

Manipulation of the push/pull wire 62 via the proximal wire port 20 in FIG. 1A may result in flexion of the distal end 35 of the catheter 25. The guidewire 57 may extend through the delivery lumen 55 which lies interior to the catheter tube 40. The push/pull wire 62 may extend through the push/pull wire lumen 60 and may be attached to radio-opaque band 67, which may surround the catheter distal end 65 and may be made of a variety of radio-opaque material such as stainless steel, platinum, gold, nickel, etc. The hinge region 58 at which the distal catheter tip 65 flexes due to proximal manipulation of the push/pull wire 62 may be located proximal to, within, or distal to the balloon (if used), as displayed respectively in FIGS. 2A, 2B, and 2C. Although the inclusion of a balloon with the catheter assembly is described herein, the balloon is optional and may be omitted entirely from the catheter assembly.

Figure 2A:
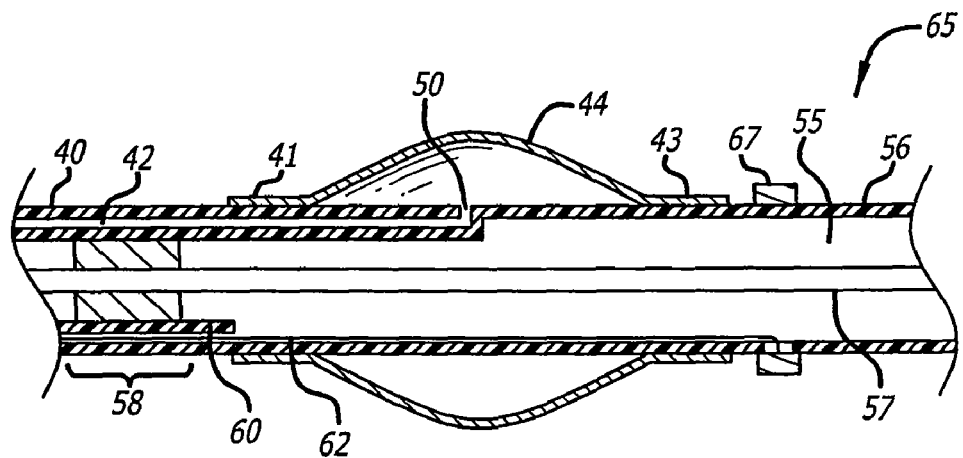
FIG. 2A shows a cross sectional view of a proximally placed hinge region in a variation of the distal region of the catheter assembly.
Figure 2B:
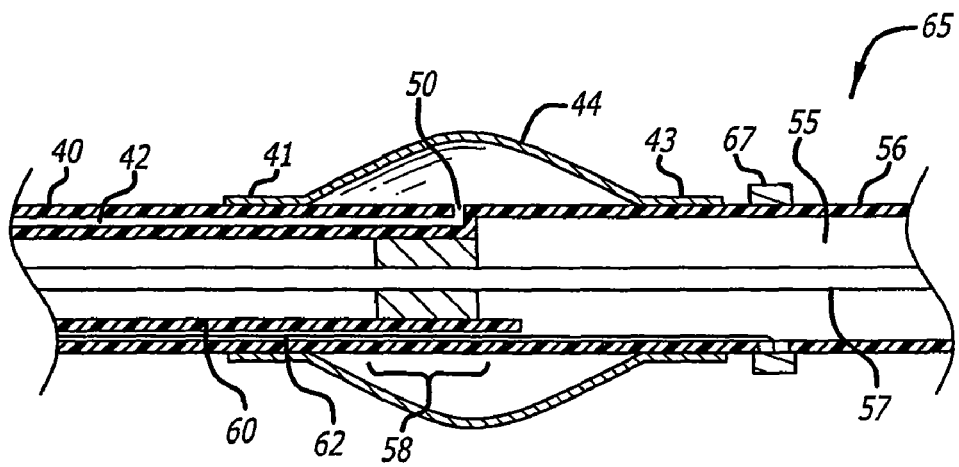
FIG. 2B shows a cross sectional view of a mid-balloon hinge region placement for another variation of the distal region of the catheter assembly.
Figure 2C:
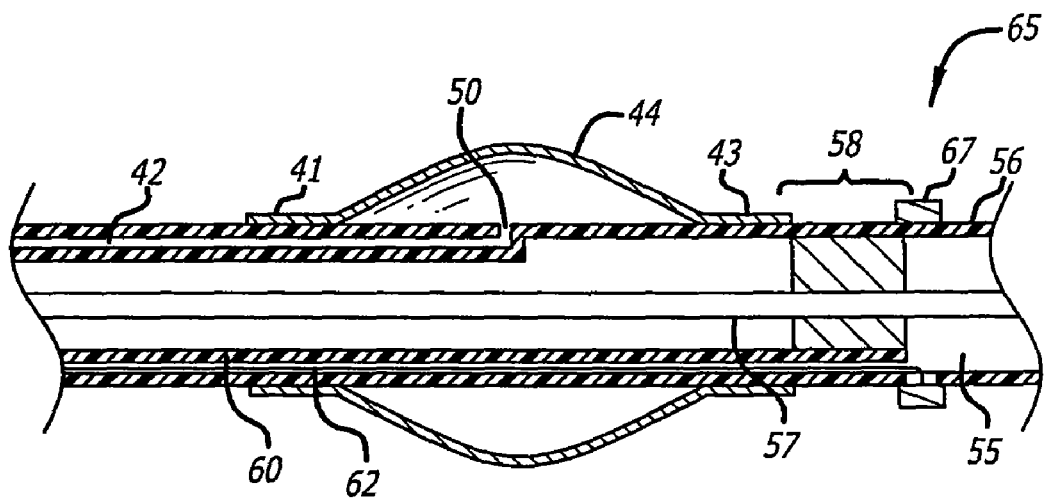
FIG. 2C shows a cross sectional view of a distally placed hinge region in another variation of the distal region of the catheter assembly.

As shown in FIG. 2A, when the hinge region 58 is placed proximally of the balloon 44, the push/pull wire lumen 60 extends to a region which is proximal of the distal end of the balloon 44 to allow flexion of the region of the catheter's distal end 65 which includes the entire balloon 44. If the hinge region 58 is placed interior to the balloon, as in FIG. 2B, flexion of the catheter's distal end 65 occurs such that the point of flexion is within the balloon (also displayed in FIG. 1B). FIG. 2C shows the placement of hinge 58 distal to the balloon; flexion during distal-hinge placement occurs such that the manipulatable region of the catheter's distal end 65 does not include any portion of the balloon 44.

Figure 2D:
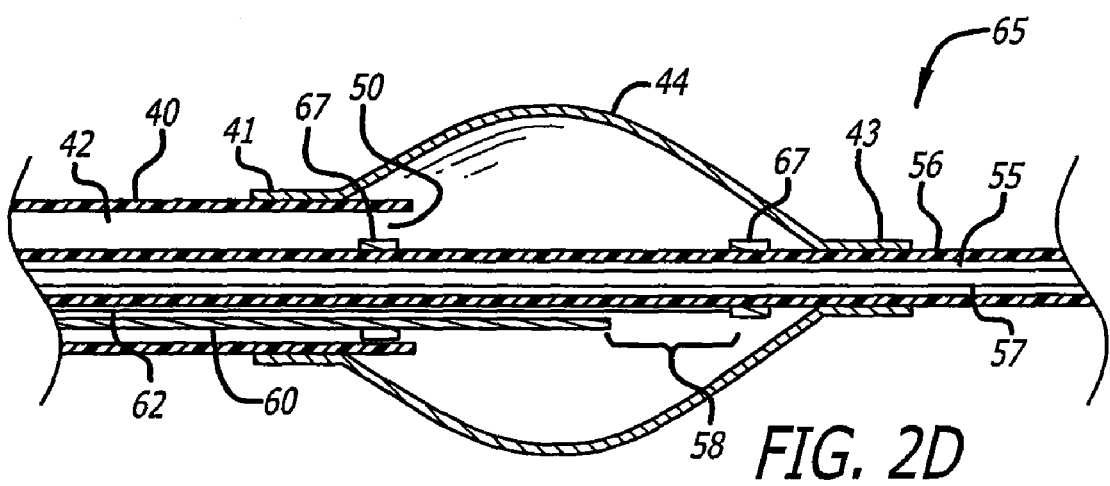
FIG. 2D shows a cross sectional view of an additional mid-balloon hinge region placement for another variation of the distal region of the catheter assembly.

FIG. 2D shows placement of the hinge region 58 interior to the balloon 44. The balloon 44 extends between the guidewire/delivery tube 56 and the outer catheter tube 40 enclosing the annular inflation lumen 42. The push/pull wire 62 is attached to the distal end 65 of the guidewire/delivery lumen tube 56. In each of the variations shown in FIGS. 2A to 2D, the push/pull wire 62 may be attached at its distal end to the catheter through a variety of methods, e.g., adhesives, crimping, mechanical fasteners, etc. In this variation, a radio-opaque marker band 67 may be used to anchor the wire 62. Moreover, other attachment sites for attachment of the push/pull wire 62 distal to the hinge region 58 will be apparent. The push/pull wire itself is preferably a wire which has sufficiently high column and tensile strengths such that it may be pushed or pulled along a longitudinal axis of the wire through the wire lumen without buckling or kinking. It may be fabricated into a wire having a circular cross-section, although other cross-sectional shapes may be utilized, having a diameter, for instance, ranging from 0.025 mm and higher. The push/pull wire may be fabricated from a biocompatible metallic material such as stainless steel, platinum, etc. Alternatively, the push/pull wire 62 may also include a tapered wire which has a larger diameter at or near its proximal end and a smaller diameter at or near its distal end. Conventional guidewires may also be utilized as a push/pull wire, provided that it has an adequate diameter and sufficient column and tensile strengths desirable for manipulating the flexible distal end of the device.

In FIG. 2D, extension of the delivery lumen tube 56 beyond the end of the inflation lumen 42 allows remote manipulation of the catheter's distal end 65 if the push/pull wire 62 is attached to the catheter using, e.g., markers or platinum bands 67. The delivery tube lumen 56 may be made of any of the above materials with respect to tube 26 in FIG. 1.

Figure 3A:
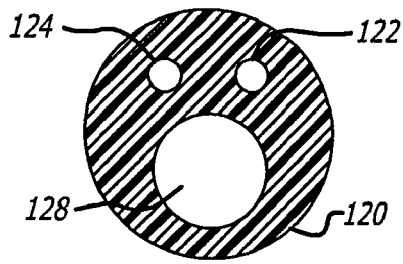
FIGS. 3A-3H are cross-sectional views of catheter shafts displaying the various relative positions of the push/pull wire lumen, main lumen, and optional inflation lumen.
Figure 3B:
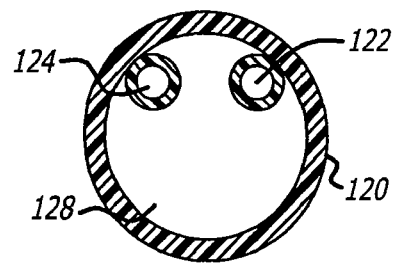

Some of the various configurations of the catheter's lumina (inflation, push/pull, delivery, etc.) are displayed in FIGS. 3A through 3H. In FIG. 3A, the optional inflation lumen 122 and push/pull wire lumen 124 are formed interior to the catheter wall 120, while the interior catheter wall forms the guidewire lumen 128. In FIG. 3B, the catheter wall 120 forms the guidewire lumen 128 which contains the optional inflation lumen 122 and push/pull wire lumen 124. The optional inflation lumen 122 is formed interior to the catheter wall 120 of FIG. 3C, while the push/pull wire lumen 124 lies within the larger coil lumen 128 (which is formed by the catheter wall 120).

Figure 3C:
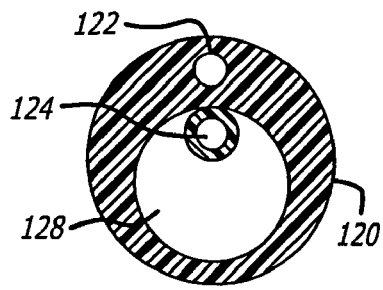
Figure 3D:
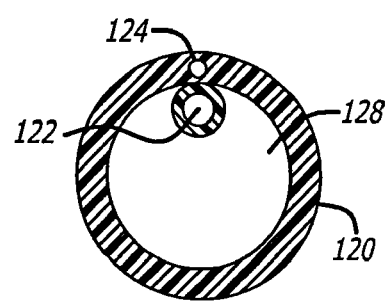
Figure 3E:
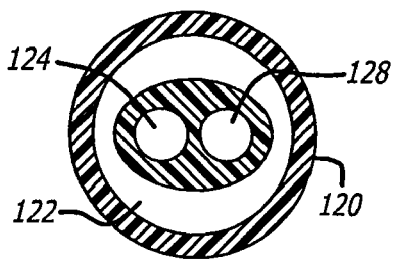
Figure 3F:
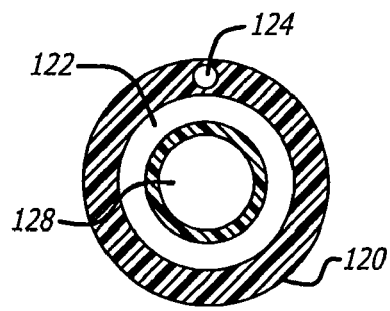
Figure 3G:
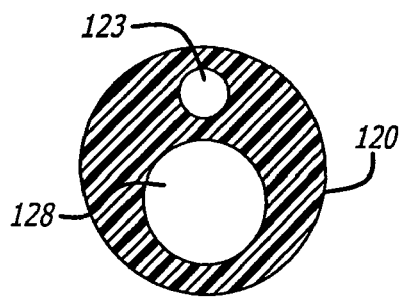
Figure 3H:
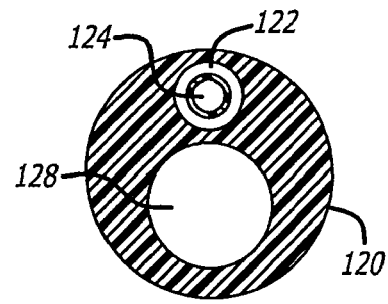

FIG. 3D is a variation of FIG. 3C in which the push/pull wire lumen 124 lies interior to the catheter wall 128 while the optional inflation lumen 122 lies within the larger main lumen 128. In FIG. 3E, the interior catheter wall 120 forms the optional inflation lumen 122, and the push/pull wire lumen 124 and the main lumen 128 are found within the inflation lumen 122. The optional inflation lumen 122 surrounds the guidewire lumen 128 and lies within the region formed interior catheter wall 120 in FIG. 3F, while the push/pull wire lumen 124 lies within the catheter wall 120. In FIG. 3G, one shared lumen 123 serves as the push/pull and optional inflation lumen; the shared push/pull and inflation lumen 123 along with the guidewire lumen 128 lie within the catheter wall 120. Another alternate variation of the lumina positioning, shown in FIG. 3H, has the push/pull wire lumen 124 lying interior to the inflation lumen 122 which is contained within the catheter wall 120, while a separate lumina for the guidewire 128 also is contained within the catheter wall.

The tube constructions, hinge region construction, and other tubing forming the various lumina discussed herein may be created through extrusion, sequential production (in which the parts are manufactured separately and later assembled together), or some other method known to one of skill in the art. Moreover, if use of the balloon is omitted from the catheter assembly, the inflation lumen may be omitted entirely as well.

FIG. 4A shows a cross-sectional side view of another variation of a catheter assembly 210. This particular variation may have a catheter body 212 with a main lumen 216 defined through the length of the assembly 210. The push/pull wire lumen 214 may also be defined through the length of the catheter body 212, or at least through a majority of the length of catheter body 212, extending from a fitting 232 at a proximal end of the catheter assembly 210 to a region near or at the distal end of the device. The catheter body 212 itself may be comprised of several regions each having a different degree of flexibility. For instance, the catheter assembly 210 may comprise a first portion 220 distal of the fitting 232 having a first stiffness. A second portion 222, having a second stiffness and located distal of the first portion 220, may be more flexible relative to the first portion 220. Likewise, a third portion 224, having a third stiffness and located distal of the second portion 222, may be more flexible relative to the first and second portions 220, 222, respectively. Thus, the catheter body 212 may have a length comprised of progressively more flexible sections the farther distally located along the catheter 212. Bending portion or flexible joint region 218 may be positioned distal to the third section 224, as described in further detail below.

The push/pull wire lumen 214 is preferably reinforced along at least a majority of its length. The wire lumen 214 may include a braided ribbon 236 integrated throughout the length of lumen 214 along catheter body length 226. Alternatively, the braided ribbon 236 may be integrated through lumen 214 to terminate proximally of joint region 218, as shown in the FIG. 4A. The braided ribbon 236 may be a uniform braid or it may be braided with a varying braid pitch. For instance, proximal sections of the catheter body 212, such as first portion 220, may have a braid which is tighter or which has a higher braid pitch than more distally located sections, such as third portion 224. If a region of lower braid pitch is flanked by regions of higher braid pitch, the region of greater pitch may generally be stiffer during manipulation of the distal catheter tip.

The braided ribbon 236 may be made from a number of materials. For instance, metals which are members of a class of alloys known as super-elastic alloys may be utilized for the braid material. Preferred super-elastic alloys include the class of nickel-titanium materials typically known as Nitinol. Other appropriate metals may also be utilized such as stainless steel or polymers may also be used such as liquid crystal polymers (LCP's). The braids which may be utilized in this invention are preferably made using commercially available tubular braiders. The term "braid" may generally include tubular constructions in which the ribbons making up the construction may be woven radially in an in-and-out fashion as they cross to form a tubular member defining a single lumen. Other braiding variations may also be utilized as typically known in the art. The braid may also be made from a suitable number of ribbons or wires. FIG. 4D shows a cross-section of catheter body 212. As shown, wire lumen 214 may have a liner 246, e.g., a lubricious polymeric liner, disposed upon the lumen wall to facilitate movement of the push/pull wire therethrough. The liner 246 may be made from any variety of suitable polymeric materials as mentioned above. Alternatively, the braided ribbon 236 may be positioned upon the inner surface of wire lumen 214. In such a configuration, a lubricious coating may be optionally omitted from the distally located portions of the device.

Although three sections of variable stiffness are described in this variation, this is intended to be illustrative. Catheters having as few as two sections or multiple (i.e., greater than three) sections of variable stiffness are also contemplated to be within this invention. Furthermore, although it is preferable to have the sections with decreasing stiffness (or greater flexibility) the further distally along the catheter body 212, other variations may include distally located sections with increasing stiffness or alternating sections of relatively stiffer and more flexible sections, or any other combinations.

First portion 220 may, for example in one variation, have a typical length of about 100 cm (±1 cm) with a stiffness or relative durometer hardness value of 72 D. The second portion 222 may have a length of about 30 cm (±1 cm) with a lower stiffness or hardness of 63 D. Third portion 224 may likewise have a length of about 30 cm (±1 cm) with an even lower stiffness or hardness value of 40 D. In either case, the main lumen 216 may be defined by a tubing having a stiffness or relative hardness of, e.g., 63 D, encased throughout the length of the device. Each of the sections are preferably integral with adjacent sections. The variable stiffness may be effected through one of any variety of methods generally known in the art, e.g., different sheaths or coverings having differing stiffnesses. For instance, PEBAX (Atochem Corporation of France) or any other polymeric material mentioned above, having the variable stiffnesses may be utilized to cover the respective sections.

The manipulatable or flexible joint region 218 is generally located at the distal end of the catheter body 212 and is configured to bend when manipulated by the push/pull wire. Flexible joint region 218 may be configured to have a length ranging from, e.g., 3 mm to 3 cm. As mentioned above, the braided ribbon 236 may terminate proximally of the flexible joint region 218. The bending portion 218 itself may be varied to extend to where braid 236 terminates, or it may be extended to bending portion 228 to encompass a portion of the braid 236. The flexible joint region 218 may be covered by PEBAX, or any other polymeric material mentioned above, having a stiffness or hardness of, e.g., 25 D, which is lower than a stiffness of third portion 224.

As mentioned above, the proximal portion of the catheter body 212 may be attached to fitting 232. Fitting 232 may be any variety of fitting typically utilized with intra-luminal catheters. In this variation, fitting 232 may define an opening 234 which is in communication with main lumen 216 to allow for the passage of guidewires, various tools, therapeutic drugs, etc. It may also be configured to accept a separately manufactured push/pull wire handle 238 with a control 240 for manipulating the push/pull wire distally or proximally along a longitudinal axis of the wire. Alternatively, the push/pull wire handle 238 may be formed as an integrated piece with fitting 232. Although the figure shows the inclusion of opening 234 in the proximal end of fitting 232, other variations may include rapid-exchange (RX) type catheter designs having guidewire lumen openings defined along the body of catheter body 212 itself.

The distal end of flexible joint region 218 may have a portion of the tubing defining the main lumen 216 extending as an extension 230 past distal face 242 of joint region 218, as shown in the detail side view of FIG. 4B. The length of extension 230 may be configured to extend at various lengths from a relatively short length to a relatively longer length, depending upon the desired bending results. Extension 230 may have a relative stiffness or hardness value, e.g., 63 D, which is higher than the stiffness or hardness of the section located proximally, i.e., flexible joint region 218. Moreover, an additional coating may be disposed over extension 230 and any marker bands or wires positioned thereon to encase the assembly, as described in further detail below. An end view of flexible joint region 218 is shown in FIG. 4C, which illustrates the variation of push/pull wire lumen 214 formed adjacently to main lumen 216. As shown, main lumen 216 may have a lubricious liner 244 defined upon an inner surface of main lumen 216 to facilitate the insertion or removal of guidewires and/or other tools through the main lumen 216. Liner 244 may be formed from any variety of suitable polymeric materials, as described above.

Figure 5A:
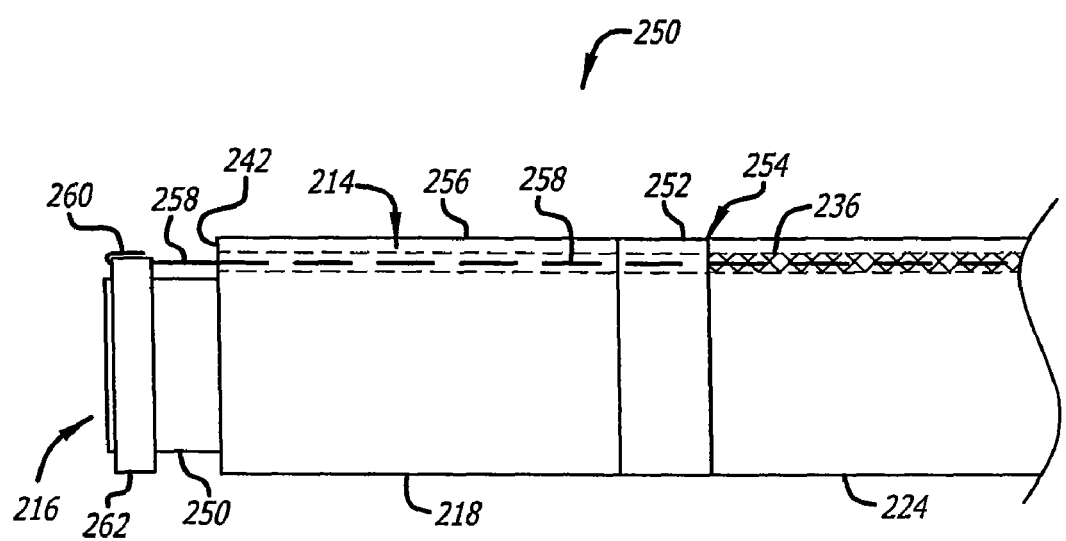
FIG. 5A shows an assembly side view of the distal portion of a variation of the catheter assembly.

Returning to FIG. 4B, tubing extension 230 may extend for a short distance past distal face 242, for instance, about 0.15 cm. As shown in the side view of distal portion 250 in FIG. 5A, a radio-opaque marker band 262, as mentioned above, may be attached over and/or onto extension 230. The push/pull wire 258 positioned within wire lumen 214 may extend through an opening in distal face 242 and attach to marker band 262. Push/pull wire 258 may be attached by being routed between band 262 and extension 230 and bent around 260 marker band 262. Alternatively, additional marker bands may be positioned upon extension 230 and used to sandwich the push/pull wire 258 between the respective marker bands. Other variations for attaching the wire 258 to the marker band 262 may also be utilized as generally known in the art. The portion of extension 230 past marker band 262 may be left or it may alternatively be trimmed flush against the marker band 262. An additional marker band may be positioned about the push/pull wire lumen 214 to aid in positional orientation of the catheter under an imaging system, such as a fluoroscope.

The flexible joint region 218 may flex beginning where braiding 236 terminates 254. Flexible joint region 218 may also incorporate an optional transitional joint region 252 between the flexible joint region 218 and the remainder of the catheter body. This transition region 252 may have an intermediate flexibility between that of joint region 218 and the catheter body or it may be configured to be more flexible than either region to facilitate bending of the region. Flexibility may be imparted to region 252, at least in part, by omitting any liners or coatings from the main lumen 216 and/or the wire lumen 214 along this region 252. In either case, the transition region 252 may be omitted entirely. The covering or sheath 256, which is preferably hydrophilic and may be disposed over the entire device or portions of the device, may also be omitted from the flexible joint region 218. This covering 256 may also be included or omitted entirely from the transitional joint region 252, depending upon the desired results. Optionally, the distal portion of the device (optionally including the joint region 252), perhaps 35 to 50 cm, may be covered with the hydrophylic coating, again depending upon the desired results.

Figure 5B:
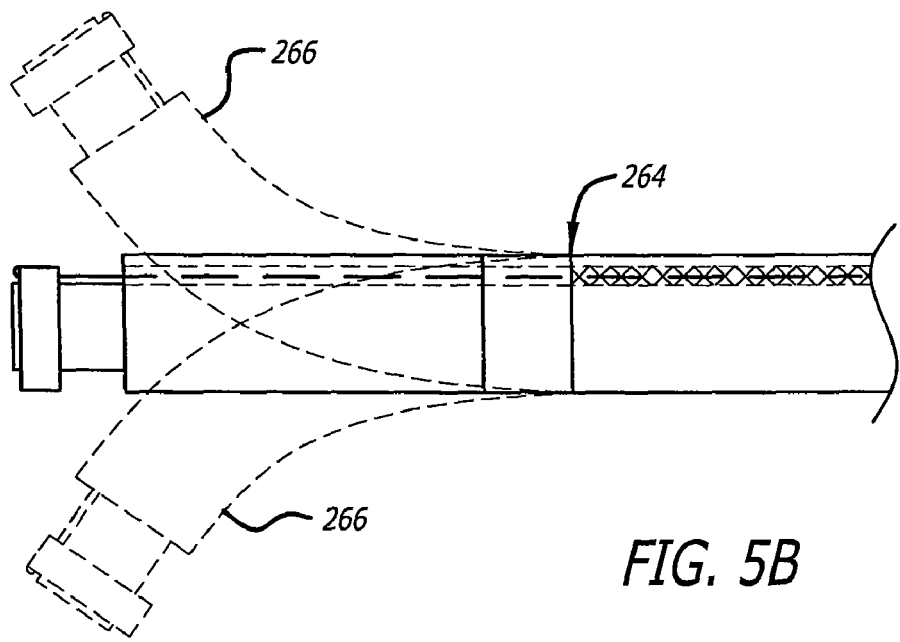
FIGS. 5B and 5C show bending of the flexible joint regions of catheters having differing lengths of the flexible joint regions.
Figure 5C:
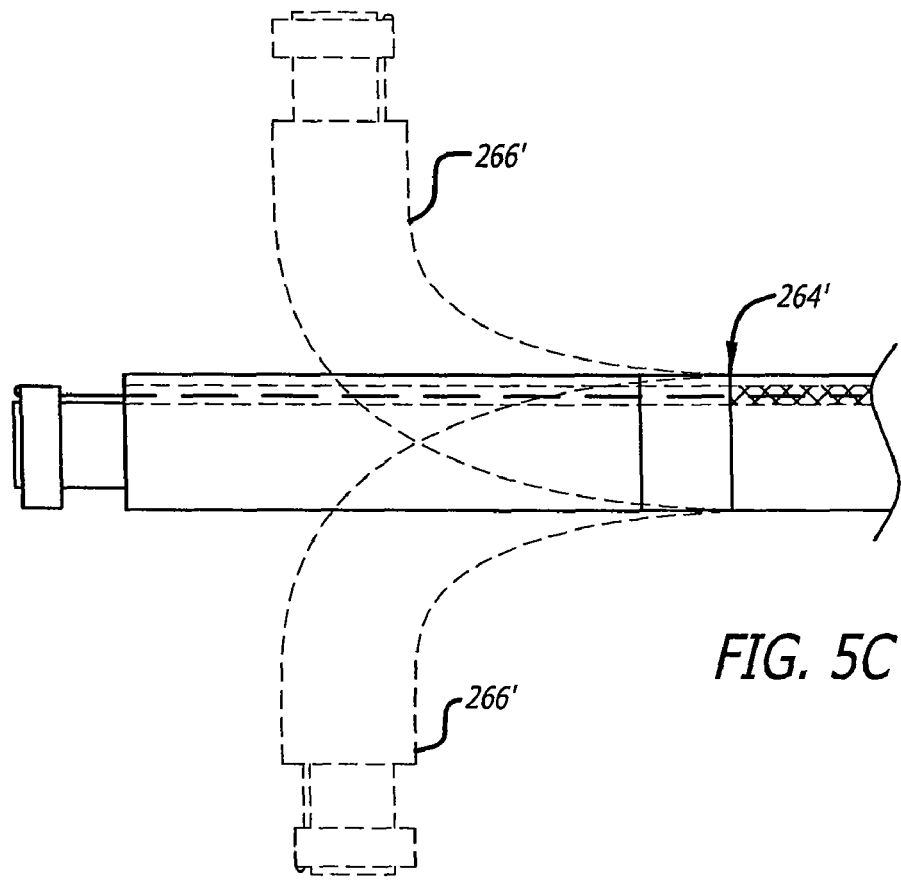

By varying the length of flexible joint region 218, the amount of curvature and flexure of the joint region 218 can be controlled. For instance, a joint region having a relatively shortened length between the distal end of the joint region 218 and the terminal end 264 of the braid, as shown in FIG. 5B, may allow for a reduced degree of flexure 266 relative to a neutral position of the catheter. In comparison, as shown in FIG. 5C, a lengthened joint region extending to a more proximally located terminal end 264' may allow for a relatively greater degree of flexure 266' relative to the flexure shown by the catheter in FIG. 5B. Accordingly, the degree of flexure may be controlled in part by the length of the flexible joint region. Thus, the flexible region may be flexed up to 90° relative to the longitudinal axis of the catheter assembly and in some cases, the flexible region may be flexed up to 180° relative to the longitudinal axis depending upon the length of the flexible joint region. To further facilitate bending of the catheter, additional members such as coils may be incorporated into the device, for instance in the transitional region, to aid in further controlling the bending of the joint region.

Figure 6A:
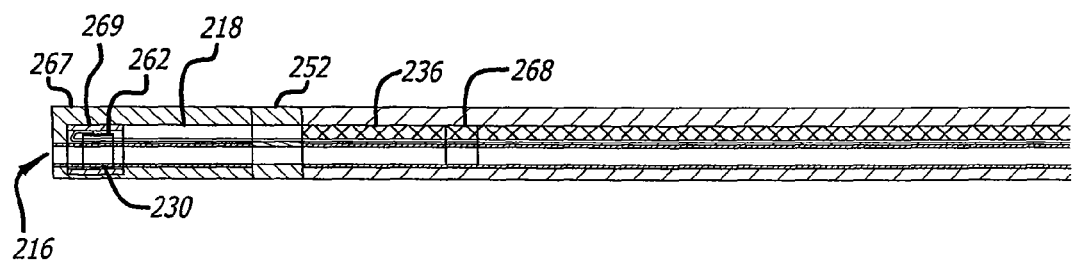
FIGS. 6A and 6B show cross-sectional side and detail side views, respectively, of another variation of the device where the distal end may be fused down by a liner.
Figure 6B:
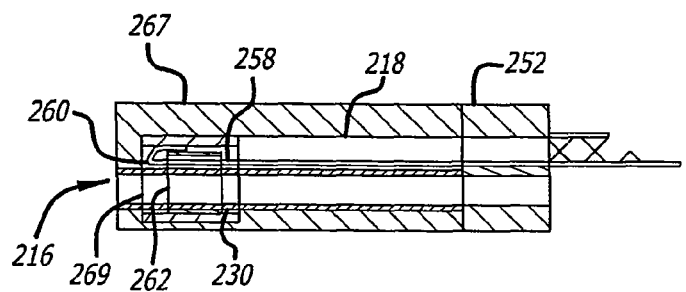

As mentioned above, the distal flexible joint region 218 may have a coating or liner 267, preferably one that is hydrophilic for ease of use within a body, disposed over it and over extension 230 to encase the assembly, as shown in the cross-sectional side view of FIG. 6A. In this variation, marker band 262 may be disposed over the extension 230 and a second marker band 269 may be disposed thereupon with the push/pull wire 258 locked in between. In this variation, second marker band 269 is larger in diameter as well as length than marker band 262; however, other sizes and configurations known to one of skill in the art may be utilized. The liner 267, which may be fused down over the entire length of the joint region 218 or just a portion of the region 218, may be made of any variety of materials described herein. The marker bands 262, 269 may be utilized to facilitate visualization of a position of the distal end of the device. Optionally, a third marker band 268 may be positioned along the device proximal to the joint region 218 to aid in visualizing potential coiling of the device.

In order to control the advancement or retraction of the push/pull wire, which controls the flexure of the flexible joint region, a variety of controls may be utilized. FIGS. 7A to 7C show side, end, and partially removed side views, respectively, of one variation of a control handle. A push/pull wire guide 270 may extend from handle 238 for transitioning the push/pull wire to the catheter. As shown in the side view of FIG. 7C, which shows handle 238 partially removed for clarity, wire control 240 is configured as a wheel which further defines a concentrically configured gear 272, as shown in FIG. 7D, which may engage with the engagement teeth 276 of rack 274, as shown in FIG. 7E. The push/pull wire may be attached to the rack 274 so that as control 240 is rotated, rack 274 may be advanced proximally or distally to thereby translate the attached push/pull wire along the longitudinal axis of the wire.

Figure 8:
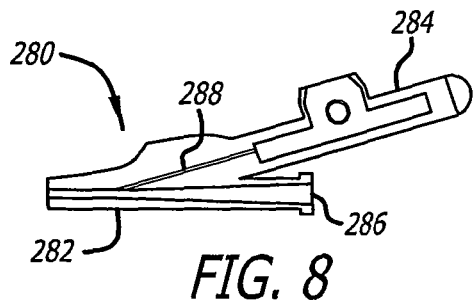
FIG. 8 shows another variation in the cross-sectional side view of combination fitting/handle assembly.
Figure 9:
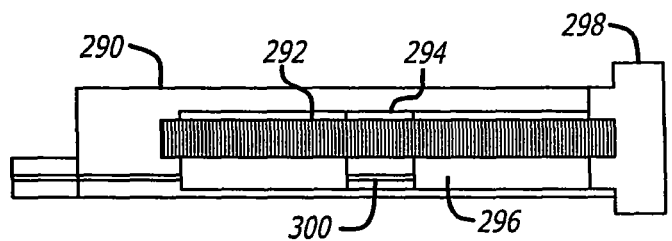
FIG. 9 shows another variation in the cross-sectional side view of the handle body utilizing a carriage screw.

FIG. 8 shows another variation in the cross-sectional side view of combination fitting/handle assembly 280. Handle body 282 may incorporate the push/pull handle portion 284 as an integrated part of a fitting. The assembly 280 may include a main lumen access 286 as well as a push/pull wire access 288. FIG. 8 shows a cross-sectional side view of another variation in handle body 290. In this variation, a carriage screw 292 may be positioned within the handle 290 such that a wire carriage 294 is configured to travel within advancement channel 296 defined within handle 290. A proximal end of carriage screw 292 may be attached to a control knob 298, which may be rotated to advance either proximally or distally the carriage 294 and the push/pull wire, which may be attached to carriage 294 at push/pull wire attachment 300.

Figure 10:
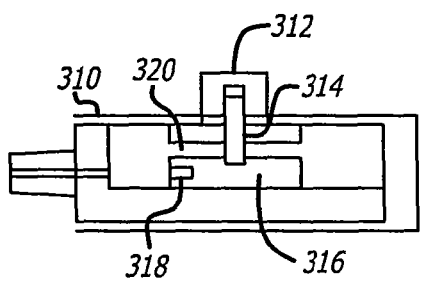
FIG. 10 shows another variation in the cross-sectional side view of the handle body utilizing a control/release knob.
Figure 11:
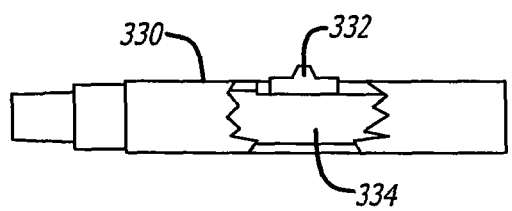
FIG. 11 shows another variation in the cross-sectional side view of the handle body utilizing a control slide.

In yet another variation in FIG. 10, handle body 310 may incorporate a control/release knob 312 which is attached to a release screw 314. The screw 314 may be attached to a wire carriage 316, which may attach to push/pull wire via attachment 318. As the knob 312 is translated proximally or distally, carriage 316 may travel within channel 320 to either advance or retract the attached push/pull wire. Knob 312 may be tightened about screw 314 against handle 310 to lock a position of the push/pull wire during flexure, if desired. In yet another variation in FIG. 11, handle body 330 may have a control slide 332 configured to proximally or distally advance a wire carriage 334 within handle 330.

The applications of the inventive catheter discussed above are not limited to certain treatments, but may include any number of vascular maladies. Modification of the above-described methods for carrying out the invention, and variations of the mechanical aspects of the invention that are obvious to those of skill in the mechanical and guide wire and/or catheter arts are intended to be within the scope of the claims. Moreover, various combinations of aspects between examples is also contemplated and is considered to be within the scope of this disclosure.

We claim:

1. A long nose manipulatable catheter section comprising:
a flexible joint region having a distal face, the flexible joint region defining a wire lumen and a main lumen therethrough, and the wire lumen having an opening from the flexible joint region near or at the distal face of the flexible joint region;
a braid disposed along at least a majority of the wire lumen of said flexible joint region, wherein said braid terminates proximally of the flexible joint region;
the flexible joint region including tubing defining an extension of the main lumen beyond the distal face of the flexible joint region;
the extension containing at least one radio-opaque band; and
a push/pull wire positioned within said wire lumen and configured to be pushed or pulled through the wire lumen, said push/pull wire having a distal portion extending through said opening of said wire lumen beyond the distal face of the flexible joint region, and said distal portion of said push/pull wire being secured to said at least one radio-opaque band.

2. The long nose manipulatable catheter section of claim 1 wherein the main lumen further comprises a lining along at least a majority of the main lumen.

3. The long nose manipulatable catheter section of claim 2 wherein the lining of the main lumen comprises a lubricious lining.

4. The long nose manipulatable catheter section of claim 1 wherein the wire lumen further comprises a lining along at least a majority of the wire lumen.

5. The long nose manipulatable catheter section of claim 4 wherein the lining of the wire lumen comprises a lubricious lining.

6. A long nose manipulatable catheter section comprising:
a flexible joint region having a distal face, the flexible joint region defining a wire lumen and a main lumen therethrough, the wire lumen including a braid disposed along at least a majority of the wire lumen, said braid terminating proximally of the flexible joint region, and the wire lumen having an opening from the flexible joint region near or at the distal face of the flexible joint region;
the flexible joint region including tubing defining an extension of the main lumen beyond the distal face of the flexible joint region;
the extension containing at least one radio-opaque band; and
a push/pull wire positioned within said wire lumen and configured to be pushed or pulled through the wire lumen, said push/pull wire having a distal portion extending through said opening of said wire lumen beyond the distal face of the flexible joint region, and said distal portion of said push/pull wire being secured to said at least one radio-opaque band.

* * * * *